(12) United States Patent
Kokoš

(10) Patent No.: US 9,731,145 B2
(45) Date of Patent: Aug. 15, 2017

(54) DEVICE FOR STIMULATION OF THE BRAIN BY LASER CIRCULARLY OR ELLIPTICALLY POLARIZED LIGHT

(71) Applicant: František Kokoš, Revúca (SK)

(72) Inventor: František Kokoš, Revúca (SK)

(*) Notice: Subject to any disclaimer, the term of this patent is extended or adjusted under 35 U.S.C. 154(b) by 228 days.

(21) Appl. No.: 14/267,054

(22) Filed: May 1, 2014

(65) Prior Publication Data

US 2014/0330350 A1   Nov. 6, 2014

(51) Int. Cl.
*A61N 5/06* (2006.01)
*A61N 5/067* (2006.01)
*A61N 5/073* (2006.01)

(52) U.S. Cl.
CPC ...... *A61N 5/0622* (2013.01); *A61N 2005/067* (2013.01); *A61N 2005/0643* (2013.01); *A61N 2005/073* (2013.01)

(58) Field of Classification Search
CPC .................. A61N 5/062; A61N 5/0616; A61N 2005/0648; A61N 2005/073
USPC ..................................................... 607/88–92
See application file for complete search history.

(56) References Cited

U.S. PATENT DOCUMENTS

| | | | | |
|---|---|---|---|---|
| 2006/0287695 A1* | 12/2006 | DiMauro | ............. | A61N 5/0603 607/88 |
| 2009/0319008 A1* | 12/2009 | Mayer | ................. | A61N 5/0603 607/90 |
| 2012/0245659 A1* | 9/2012 | Matthews | ............ | A61N 5/0601 607/89 |
| 2014/0358199 A1* | 12/2014 | Lim | ..................... | A61N 5/0603 607/92 |

* cited by examiner

*Primary Examiner* — Lynsey Eiseman
*Assistant Examiner* — Dacheng Xie
(74) *Attorney, Agent, or Firm* — Minder Law Group; Willy H. Wong

(57) ABSTRACT

The device intended for the stimulation of the brain by laser circularly or elliptically polarized light consists of the main unit (1) equipped in the front part with control buttons (3), and a display (2) from which at least one laser diode (16, 17, 18, 19) is supplied. At least one nasal applicator (8, 9, 10, 11) or nasal applicators (38, 39) suitably equipped in the rear part with laser diodes (40, 41) can be connected to the upper part of the main unit (1). The main unit (1) is supplied in its lower part through a connector (33), and the programmable control unit (51) with built-in battery (56) and autonomous processor (57) is an integral part of the device.

17 Claims, 7 Drawing Sheets

DEVICE FOR STIMULATION OF THE BRAIN BY LASER CIRCULARLY OR ELLIPTICALLY POLARIZED LIGHT

RELATED APPLICATIONS

This application claims priority to Slovakia Patent Application No. PUV 76-2013, filed on May 3, 2013.

FIELD OF THE INVENTION

This invention relates to devices used for the stimulation of the brain, more specifically stimulation of the brain by laser circularly or elliptically polarized light applied through the nasal cavity. This invention also relates to devices for the irradiation of the nasal cavity by laser light for the purpose of affecting the condition of the blood.

BACKGROUND OF THE INVENTION

Devices that are currently used for the stimulation of the brain use audiovisual stimulation, whereby the brain is stimulated by sound signals entering the ears and/or by visual stimulation using spectacles with LED diodes or patterns on a screen in front of the eyes of a treated person. The brain can also be stimulated using sources of magnetic fields near or in contact with the scalp of the head, while fields are changed according to a program that controls their alteration. Devices using visual stimulation by bright white lights flashing with adjusted frequencies sent to the area of aural holes are also used. All used solutions focus on the stimulation of the brain with frequencies from external sources.

The subcranial area or nasal cavity and their irradiation are not used for the stimulation of the brain by any of the aforementioned devices. Nerve cells respond to signals in the acupuncture field on the skin, and according to the research of Reininger, Bahr, and Nogier, frequencies up to approximately 5,000 Hz are used. Many devices using frequencies up to 10,000 Hz are manufactured, and responses of the organism to the stimulation of biologically active points on the body surface, for example along nerve paths, are achieved by their applications. This creates prerequisites for the effective use of such frequencies in the area of the nasal cavity and subcranial pit, with a large number of acupuncture points. Frequencies are applied to acupuncture points on the skin in the form of electrical signal or laser light, usually on the surface of the skin or just under the skin, near a biologically active point, but they are not applied to mucous membranes in the nasal cavity or to tissues in the subcranial pit, where light is a suitable carrier of frequency signal. It is stated that by affecting the frequencies of the brain, when the brain follows external stimuli, the adaptation and synchronization of neurons can be trained in such a way that they would also work on different frequencies, as are usually used in the brain area. In this way, objectives in the field of the prevention and treatment of disease, sensations, perceptions, thinking, and acting can be achieved, and this in a manner capable of affecting memory capacity, response ability, and some sources demonstrate the influence of human intelligence.

Devices based on LED diodes and laser diodes are used for the irradiation of the nasal cavity. Devices for the irradiation of the nasal cavity based on LED diodes, in contrast to laser diodes, do not demonstrate a sufficient ability to affect the blood, and indications for the use of LED diodes are limited to rhinitis, sinusitis, and problems in the area of the nose cavities and frontal sinuses. Systems with laser diodes are intended for the improvement of blood properties, and work with differently-shaped lights directed to the nasal cavity for the purpose of affecting blood properties. At the present time, irradiation of the nasal cavity is not connected with means for the stimulation of the brain by frequencies of wider bans. If frequencies are used, they are very low, as a rule up to 1-2 Hz, with effects near those of continuous light, and objectives in the field of the use of wider frequencies are not followed that are similar to the methods of audiovisual stimulation or acupuncture with impacts on the brain and treatment of a spectrum of other diseases that lead to further effects. Applications of light in the nasal cavity are limited to only red color, within the range of approximately 632 to 670 nm. The level of polarization at output from the device is considerably different.

The main objective of currently manufactured devices is to achieve an improvement of blood parameters, and influence the congestion of an organism, and cardiovascular and cerebrovascular diseases as consequences of hyperlipidaemia and increased blood viscosity. The nasal applicator device is for the transmission of laser light to the nasal cavity. It is usually made of plastic. A laser diode is the source of light that could be located in the applicator, and light is transmitted to the nasal cavity, either directly or through a short optic fiber. Or light is transmitted to the applicator through an optic fiber, while this optic fiber can pass through the entire length of the applicator, or a connector of optic fibers will be used in the applicator; light is transmitted to the nasal cavity through a short section of optic fiber that is an integral part of the applicator. If optic fibers are used in the design, light is affected by these fibers, and usually it is not linearly polarized light at output, which is a disadvantage if the laser diode emitting light directly to the nasal cavity is used; such light is only linearly polarized, which is a disadvantage.

Based on the construction of the applicator, its next part behind the laser diode that can be called an intermediate piece is inserted into the applicator, or it is slipped over the applicator. The intermediate piece and the applicator can be connected by sticking, sealing, or tightening nut or by clamping connection tightened by a nut, or the intermediate piece is screwed on the applicator or screwed into the applicator. The connection of these two pieces can be different. Light can be transmitted through the center of an intermediate piece by an optic fiber, or light passes through the center of an intermediate piece without an optic fiber. The applicator can be inserted into the nasal cavity with an intermediate piece, but usually the nasal adaptor can be slipped over the intermediate piece with a small hole on the top. If the intermediate piece and the nasal applicator are firmly connected, an additional cover in the case from silicone can be used, either with or without a small hole on the top. This is so-called external protection, and can be slipped over the adaptor, or directly over the intermediate piece. Both the intermediate piece and the nasal adaptor can be dismantled using the screwed connection, or by slipping over, or they can be firmly connected by pressing, sticking, or sealing.

Removable or firmly connected nasal clips can be connected to the applicator to keep the applicator in the nose, in order that the applicator could be used without the necessity to hold it by the hand in the nostril, or the applicator is held by a cable run behind the ear. In this case, light enters the nostril, and the cable is run to the applicator from the lower side of the applicator. Applicators of the aforementioned designs generate light with wave lengths produced by laser sources. Light of red color is used worldwide. It is usually produced by laser diodes. Generated light consists of beams with a different number of reflexes when propagated through optic fibers of different diameters, therefore lights from devices are of different shape, while laser diodes with various characteristics of irradiation, different light divergence in the direction of polarization and in the direction perpendicular to polarization are used, and light emitted from a device varies for different devices by the degree of polarization that is a substantial property of light. This is a disadvantage of the currently manufactured and used devices, because lights with different degrees of polarization are used, which enter the nasal cavity. Therefore different effects can be achieved from applications.

A disadvantage of existing devices is that these devices cannot generate light with a high degree of polarization, in the best case of circular polarization that is more stable in soft tissues as linear polarization or elliptical polarization, while elliptical polarization has properties ranging between linear and circular polarization. A disadvantage of the currently manufactured devices is that these devices use only linear polarization, while degree of polarization is different for different devices, and therefore effects on humans can also differ. The aforementioned facts represent the considerable limitations of the nasal cavity laser irradiation method, as well as the effects achieved from the point of view of used frequencies of intermittent light, wave lengths, and light polarization.

SUMMARY OF THE INVENTION

It is an object of the invention to overcome the disadvantages of the prior art discussed above.

It is an object of the invention to stimulate the brain through the subcranial area or the nasal cavity.

It is an object of the invention to irradiate the nasal cavity.

It is an object of the invention to condition the blood.

It is an object of the invention to irradiate using a broad spectrum of wavelengths.

It is an object of the invention to use circularly or elliptically polarized light within the nasal cavity.

It is an object of the invention to use highly polarized light within the nasal cavity.

It is an object of the invention to provide a consistent degree of polarization.

It is an object of the invention to provide consistent irradiation, conditioning, and treatment.

It is another object of the invention to provide a simple, efficient, durable, and cost effective device to stimulate the brain.

The aforementioned deficiencies of prior art devices are remedied by the device for stimulation by laser circularly or elliptically polarized light. This device is used for application in the nasal cavity, which allows a different effect to be achieved compared with the existing devices intended for the stimulation of the brain. The device affects the properties of light immediately before the output of light from the device. In this way it creates the possibility of unambiguous definition of properties of light entering the nasal cavity, and affects tissues by using several optional types of light polarization, which was not allowed by current devices. Using the suitable polarization of light and frequencies, pulsations, or interruption of laser light only in the area of the nasal cavity, effects can be initiated from the laser irradiation of blood or the audiovisual stimulation of the brain.

The device intended for the stimulation of the brain by laser circularly or elliptically polarized light consists of a main device unit with control buttons and display. The display can be a touch screen, and the main unit can be either stationary or portable. Several types of laser diodes can be located near the main unit or in the unit. Wave lengths are within the range 400 nm to 1,300 nm. Several nasal applicators, which can be suitably equipped with laser diodes, are connected to the main unit with electrical power cables or optic fibers. All applicators include an intermediate piece. They are equipped with replaceable nasal adaptors and nasal clips. The nasal applicator or nasal adaptor can include a light plate adapter that can include a polarizer, quarter-wave plate, or polarization foil intended for the generation of circularly or elliptically polarized light and pieces of glass. Pieces of glass can have the shape of lenses for forming the shape of light and for the protection of polarizer and quarter-wave plate, which are also included between pieces of glass. The polarizer is used only if the light before the first piece of glass is not linearly polarized. If the nasal adaptor included pieces of glass, polarizer, and quarter-wave plate, then their assembly is intended for the generation of circularly or elliptically polarized light, while the type of polarization is determined by the angle of light polarization plane from polarizer to the fast optical axis of quarter-wave plate, and by matching light wave length and quarter-wave plate. The device also allows the creation of linear polarization with a high degree of light polarization, if the light at output from applicators does not have such properties.

However, the objective of the solution is to create ways for the creation of circularly polarized light and elliptically polarized light that is not currently allowed by devices. Different polarizations, such as circular right-hand or left-hand polarization or elliptical right-hand or left-hand polarization are created by the new design of the nasal applicator, or by the new construction of the nasal adaptor. Different types of polarization achieve different types of penetration that preserve the polarization, which also depends on the properties of irradiate tissue. Better results using circular polarization can be presumed in tissues such as the subcranial pit and nerve cells and blood than in the case of linear polarization, because circular polarization preserves its properties on a longer path than linear polarization in the irradiation of tissues, and in this way the volume of tissue is increased, that is, the number of nerve cells irradiated by light with more stable polarization or a higher degree of light polarization is also increased. Because the polarization of light is a substantial property, the device allows its creation just before the exiting of light from the applicator into the area of the nasal cavity, with a high proportion of polarized light exiting the device.

The nasal applicator or nasal adaptor, where the type of polarization is changed, is a new solution. The nasal adaptor can be used after the suitable modification of its geometrical dimensions and fixation to the applicator for various nasal applicators. The end part of the nasal adaptor or applicator includes either a polarizer or quarter-wave plate or both components, according to the design, which are included between pieces of glass so the cleaning of such elements is possible. Applicators or adaptors have been designed to allow light from laser diodes to exit without passage through the optic fiber, entering directly the quarter-wave plate. The laser diode must have a suitable divergence for this. It is an advantage if the applicator or nasal adaptor includes an optic device with a correctly adjusted angle of linearly polarized light from the polarizer to the fast optical axis of the quarter-wave plate, which is usually +45 and −45 degrees to achieve circular polarization. If light from the laser diode passes through an optic fiber that changes the properties of light, the polarizer sometimes with the quarter-wave plate is located on the fiber output. If the properties of light from the laser diode are not changed by its passage through optic fiber, or if the quarter-wave plate is not used, output is represented by linearly polarized light in the entire cross-section of light passing to the nasal cavity. If the quarter-wave plate is used, output is represented by circularly/elliptically right-hand or left-hand polarized light.

The simplest solution is based on the connection of polarizer and quarter-wave plate into a single layer foil located in the nasal cavity behind the optic fiber. Exiting light must have such properties that are created for it by end devices before entering the nasal cavity. The nasal adaptor can be slip-over, slipped into intermediate piece with a hollow or optic fiber, equipped with a light guide and swivel adjustable around the longitudinal axis. It can be manufactured from materials that allow chemical disinfection or a protective element can be slipped on from the outer side, manufactured from elastic medicinal silicone, with or without a small hole at its end. It can be manufactured with linear polarization, circular or elliptical, right-hand or left-hand. It can be a suitable way to increase the efficacy of light in continuous mode of light operation in devices using nasal applicators for the irradiation of the nasal cavity with laser light, this with the objective of influencing only the properties of blood in connection with the circular or elliptical polarization of light. In the case of linearly polarized light, it can usually increase the polarization degree over 99%. The nasal adaptor can be slip-over or slip-in, and swivel adjustable around the longitudinal axis against the applicator.

The smallest dimensions of the device can be achieved if light passes to the nasal applicator through an optic fiber, or if a laser diode is located in the applicator, if the device generating circular polarization is located immediately behind the laser diode and everything is firmly or separable connected in one unit. In this case, if the unit is firmly connected, the change of direction and type of polarization can be implemented by the replacement of the nasal applicator with another one, with different internal adjustments, due to the fixed adjustment inside the device. If circular polarization foil is used, or a part containing the device generating circular polarization is used together with the quarter-wave plate (but not circular polarization foil), the direction of linear polarization against fast optical axis changes from +45 degrees to −45 degrees. Polarization would be changed from circular through elliptical, linear-elliptical up to circular, while in the case of a positive angle it would be right-hand polarization, and in the case of a negative angle—left-hand polarization. If the device generating circular polarization is an integral part of a detachable part, for example an intermediate piece or nasal adaptor, the type of polarization can be changed only by the replacement of these parts. In such case, these parts of the nasal applicator must be detachable and replaceable.

The main unit of the device is supplied or charged using a cable from a network or from an adapter through a connector. The main unit allows creating programs for power outputs of laser diode and frequencies of pulsations or interruptions of light, or they are pre-programmed into it, or they are transmitted to the programmable controller from the computer, or they are created by a mobile phone application.

A programmable controller with integrated battery is part of the device, together with an autonomous processor equipped with buttons. It can be connected to the computer or mobile phone. The device intended for the stimulation of the brain with laser circularly or elliptically polarize light is characterized by the fact that if the laser diode is an integral part of the nasal applicator, then the nasal applicator, which is plastic, is connected to the main unit of the device by an electrical power cable in the lower part, in the light axis or tangentially to the light axis, or perpendicularly to the light axis. If the laser diode is located in the main unit of the device or near it, then the nasal applicator can be connected to the main unit of the device with an optic fiber.

Light power outputs usually range from 1 to 5 mW from laser sources, but correct adjustment of power output and time is necessary, i.e. the dose of light in order attenuation and suppression would not occur in the case of too high dose of light. Nasal mucous membranes are differently sensitive to different light wave lengths in each human being, so power output must take into account even this factor. Therefore power output, time and quantity of energy allow the optimum parameters of therapy to be adjusted, taking into account the sensitivity of mucous membranes. The power outputs of the device will range from 0.5 milliwatt up to several tens of mW. Accompanying phenomena of the method of stimulation of the brain by laser light, which is applied through the nasal cavity in that part which is sensitive to the effects of neurological stimulation of the brain, cause that frequencies can significantly increase the effects achieved by the irradiation of blood with laser light. The production of ATP in the brain tissue can be considerably increased when using frequencies in comparison with the use of continuous light. With some frequencies, releasing hormones such asendorphin, serotonin, and norepinephrineis increased, and the production of melatonin is affected.

An important advantage is that during the application the eye ground is also irradiated, receptors on the retina are stimulated, and a pulsating signal is transmitted through eye nerves into the area where this information is processed. Therefore the effect of this device can be much stronger than in the case of visual stimulation of the brain from the outer side of eyes, because more effects occur with a synergic effect on the achieved results. Irradiation of the exe retina from the back side can be both preventive and therapy of degenerative diseases of the retina.

The main effect of neural stimulation of the brain is based on improving the condition of patients suffering from ADD/ADHD and autism, help for people suffering from anxiety, depression, hypertension, insomnia, pain and fibromyalgia, headache and migraine pain. Behavioral disturbances and seasonal affective disorder can be affected. Improvement of the course of pre-menstrual symptoms can be demonstrated. Improvement of memory and concentration are among the results of using this device. Increased intelligence in association with the laser irradiation of the blood can be even more important than by the sole stimulation of the brain with the frequencies of current devices, and the method used worldwide can also be achieved.

DETAILED DESCRIPTION OF THE INVENTION

Figure 1:
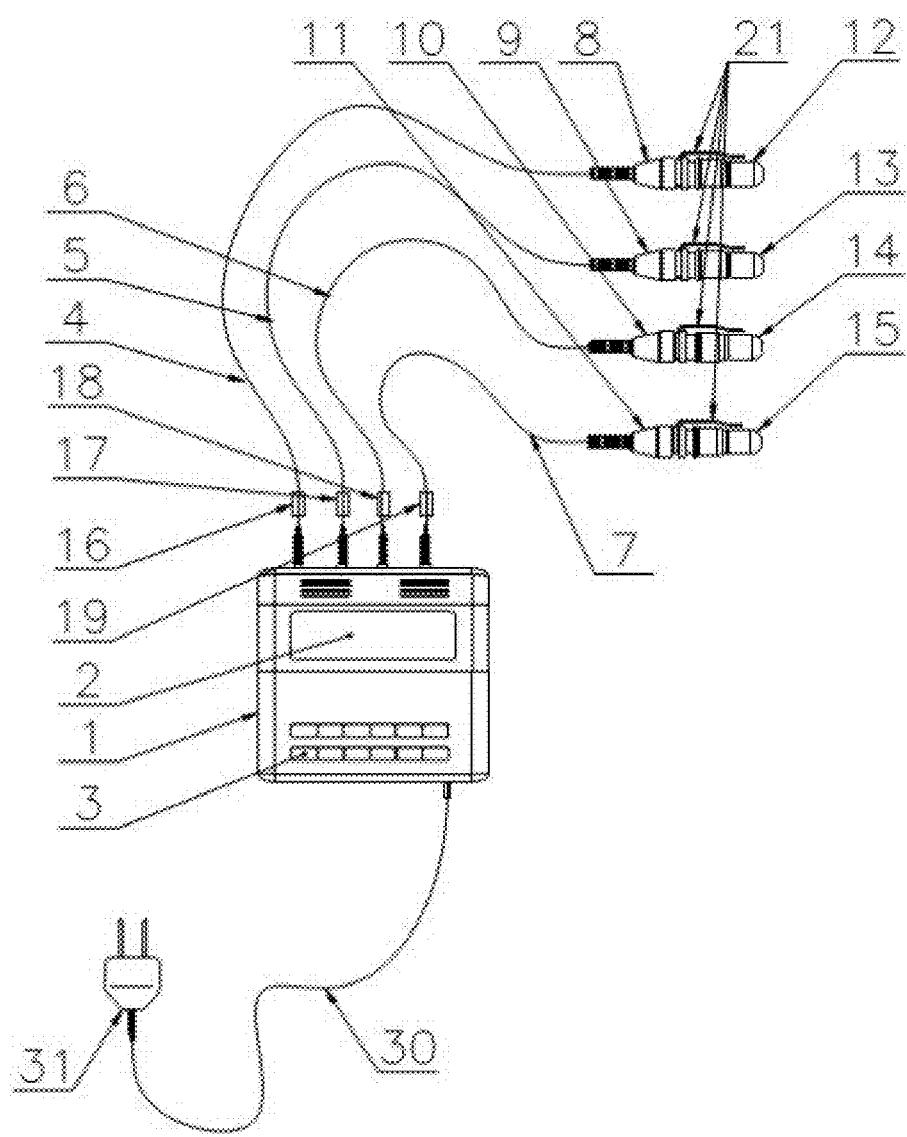
FIG. 1 illustrates one embodiment of the invention capable of being used for clinical and outpatient use.

Referring to FIGS. 1 to 10, the device consists of the main unit 1 equipped with control buttons 3 and display 2 in the front part, from which at least one of laser diodes 16, 17, 18, 19 is supplied with electric energy, and to which at least one of nasal applicators 8, 9, 10, 11 or nasal applicators 38, 39 suitably equipped with laser diodes 40, 41 in the rear part are connected in the upper part by electric power cables 36, 37 or by at least one of optic fibers 4, 5, 6, 7. All nasal applicators 8, 9, 10, 11 include an intermediate piece 110 in the central part. They are suitably equipped with at least one of replaceable nasal adapters 12, 13, 14, 15, 42, 43 in the end part at exit, and with nasal clips 21 in the peripheral part. At least one of nasal adapters 12, 13, 14, 15, 42, 43 includes polarizer 47, quarter wave plate 48, circular polarization foil 99, adhesive layer 98, and/or one of the pieces of glass 46, 49 in the end part at the exit. The main unit 1 is supplied or charged in the lower part through connector 33 using cable 30 from the mains or from adapter 32. Programmable controller 51 with built-in battery 56 and autonomous processor 57 can also be part of the device. It is equipped with button 58 in the front part, and can be connected to the computer 50 or to the mobile phone 60.

If laser diodes 40, 41 is an integral part of at least one of nasal applicators 8, 9, 10, 11, 38, 39, then at least one of nasal applicators 8, 9, 10, 11, 38, 39, suitably manufactured from plastic, can be connected to the main unit 1 with one of electrical power cables 36, 37 in the lower part, in light axis or tangentially to the light axis or perpendicularly to the light axis. If at least one of laser diodes 16, 17, 18, 19 is located in the main unit 1 then at least one of nasal applicators 8, 9, 10, 11 is connected to the main unit 1 with one of optic fibers 4, 5, 6, 7.

Polarizer 47 and quarter-wave plate 48 are included in pieces of glass 46, 49, which can have the shape of lenses for the formation of the shape of light and protection of polarizer 47 and quarter-wave plate 48 included between pieces of glass 46, 49 or they are straight.

At least one of nasal adapters 12, 13, 14, 15, 42, 43 can be slipped over or slipped into the intermediate piece 110, with hollows or optic fiber 100 equipped with light guide and swivel adjustable around the longitudinal axis. It is manufactured from materials with chemical disinfection or a protective element manufactured from an elastic medicinal silicone small hole at the end, or without the hole is slipped over from outer side.

The device is operated by buttons 3 or from touch screen, and the main unit 1 can be stationary or portable. If display 2 is a touch screen, display 2 replaces buttons 3. At least one of nasal applicators 8, 9, 10, 11 or suitably at least one of nasal adapters 12, 13, 14, 15, 42, 43 is terminated at the exit with elements for generation of linear, circular, or elliptical polarization. Polarizer 47 can be used only if the light upstream of the first piece of glass 46 is not polarized, if at least one of nasal adapters 12, 13, 14, 15, 42, 43 includes linear polarization of light, so the device does not include the quarter-wave plate 48. If at least one of nasal adapters 12, 13, 14, 15, 42, 43 includes piece of glass 46, polarizer 47, or quarter-wave plate 48, then piece of glass 46 is manufactured with circular or elliptical polarization of light, while the angle of polarization plane from polarizer 47 to fast axis of quarter-wave plate 48 and the matching of light wave length and quarter-wave plate 48 is crucial. Wave length range of at least one of laser diodes 16, 17, 18, 19 is from 40 nm to 1,300 nm. The main unit 1, computer 50, and mobile phone 60 can include the option of selection of power output of at least one of laser diodes 16, 17, 18, 19 or frequencies of pulsations or interruptions of light by mechanical control elements, such as buttons 3 or by selection of buttons on touch screen of the main unit 1 or mobile phone 60 or buttons in application in computer 50.

One embodiment of the invention according to FIG. 1 can be represented by a larger main unit 1 with a complete and complex offer of functions on display 2, control buttons 3, while if display 2 is a touch screen, it replaces buttons 3. The main unit 1 is supplied from the mains with cable 30, from socket 31 and at least one of laser diodes 16, 17, 18, 19 with a range of wave lengths from approximately 400 nm to 1,300 nm, located in the device or near the device, generates light that is conducted at least through one of optic fibers 4, 5, 6, 7 at least to one of nasal applicators 8, 9, 10, 11. One person can simultaneously use in the nose one or two applicators 8, 9, 10, 11, or two persons are simultaneously treated, while each person uses his or her applicator 8, 9, 10, 11, while one person can use two applicators 8, 9, 10, 11 in the nostrils and two applicators in the ear holes, while four persons can be treated simultaneously. Replaceable nasal adaptors 12, 13, 14, 15 are integral parts of applicators 8, 9, 10, 11. Such devices are suitable for medicinal applications in health facilities, first aid facilities, out-patient departments, and specialized work places for cardiovascular and cerebrovascular diseases and neurological work places, as well as in other applications.

Figure 2:
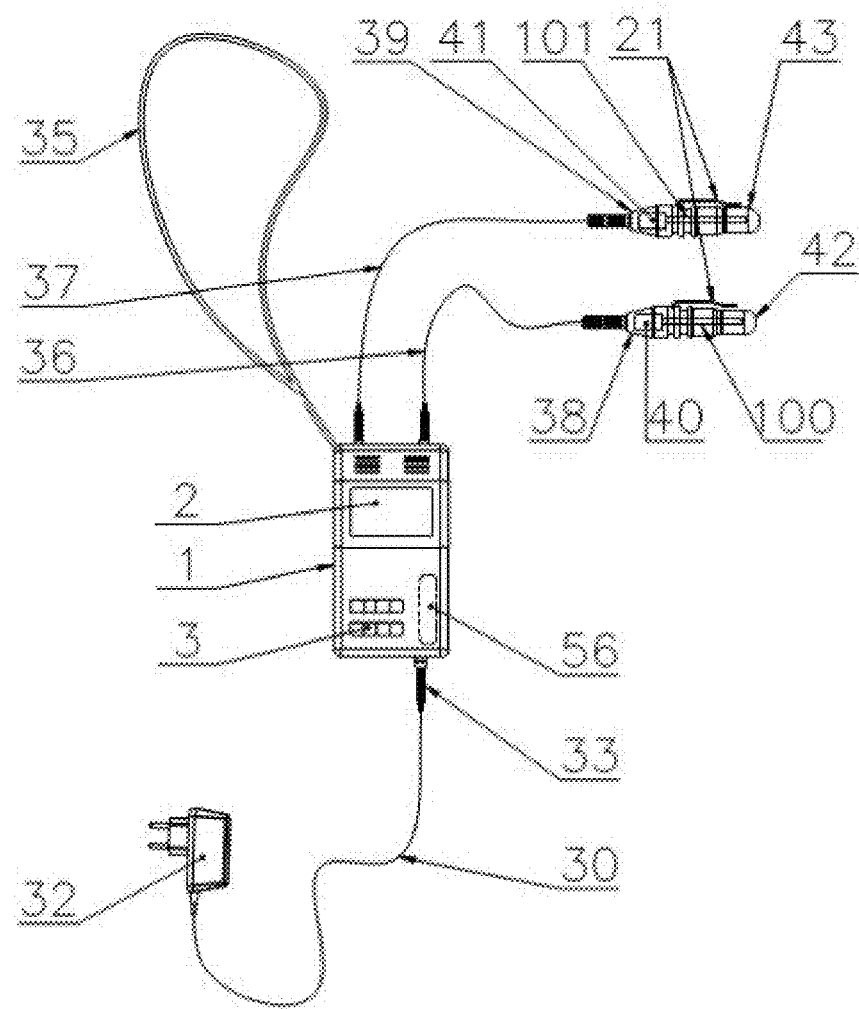
FIG. 2 illustrates one embodiment of the invention capable of being used for domestic use.

One embodiment of the invention according to FIG. 2 can be represented by a small portable device consisting of the main unit 1 with complete and complex offer of functions on display 2, control buttons 3, while display 2 can be a touch screen, and in this case it replaces buttons. The main unit 1 of device is charged from the mains by cable 30 from adapter 32 through connector 33 connected to the main unit 1. Two laser diodes 40, 41 that are located in nasal applicators 38, 39 are supplied from the device by two conductors 36, 37. Light generated by laser diodes 40, 41 passes through optic fiber 100, 101, which is run through nasal adapters 42, 43 into the nasal cavity and subcranial pit. Nasal applicators 38, 39 are used mainly in the nasal cavity, but their use for the irradiation of ear holes and tissues of internal ear is not excluded. Two persons can be simultaneously treated by the device.

Figure 3:
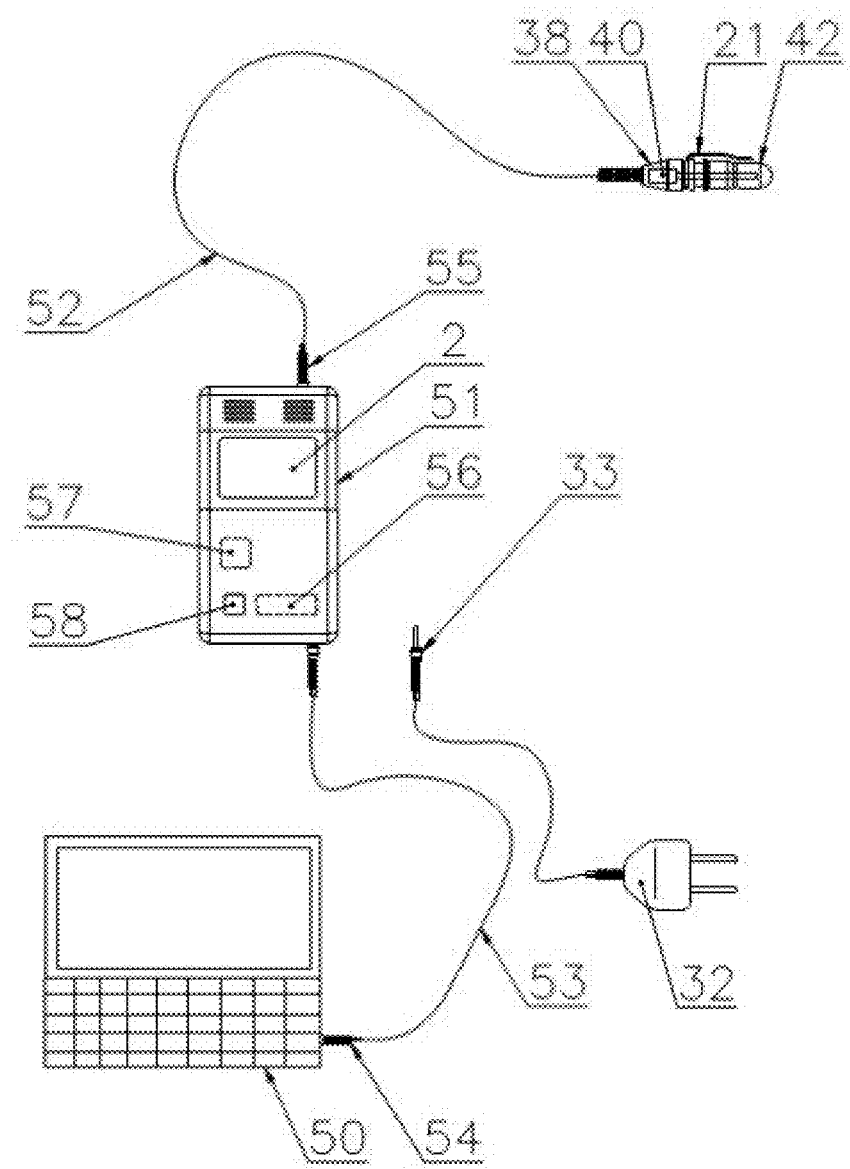
FIG. 3 illustrates one embodiment of the invention capable of being used with a computer.

One embodiment of the invention according to FIG. 3 is a small programmable control unit 51 with built-in battery 56, and autonomous processor 57 that can be connected to the computer 50. Parameters of adjustment of treatment can be stored in the programmable control unit 51 through interconnecting cable 53 that is connected to the computer 50 by connector 54 and to the programmable control unit 51 by connector 33. After finishing the programming, the programmable control unit 51 is disconnected from the computer 50, and is connected to the nasal applicator 38 through cable 52. The programmable control unit 51 has own batteries 56 and is charged either from USB port of the computer 50 or from adapter 32. Basic parameters can be seen on display 2 of the programmable control unit 51, but in the simpler case, the programmable control unit 51 does not include it, and the programmable control unit can be switched on by holding button 58 for a longer time, and it is started by holding button 58 for a short time. The application can be interrupted by pressing button 58 for a short time. The device is switched off automatically after expiration of the application time, or by holding button 58 for a longer time, or if the application is not started, the device is switched off after expiration of time adjusted in the programmable control unit 51. This design allows a physician to program the device for a patient, recommend his or her dosage by defining the daily number of applications and the time of one application, and the continuous evaluation of changes in his or her health state. Miniature size of the programmable control unit 51 and simple operation for the user are advantages. The device can be charged by a patient from adapter 32 or from port of a computer 50, and the programmable control unit 51 cannot be switched on if the battery status is below a certain value of voltage. In this case the device must be charged. The nasal applicator 38 is connected to the small programmable unit 51 by cable 52 using connector 55. It has built-in laser diode 40 and nasal applicator 42.

Figure 4:
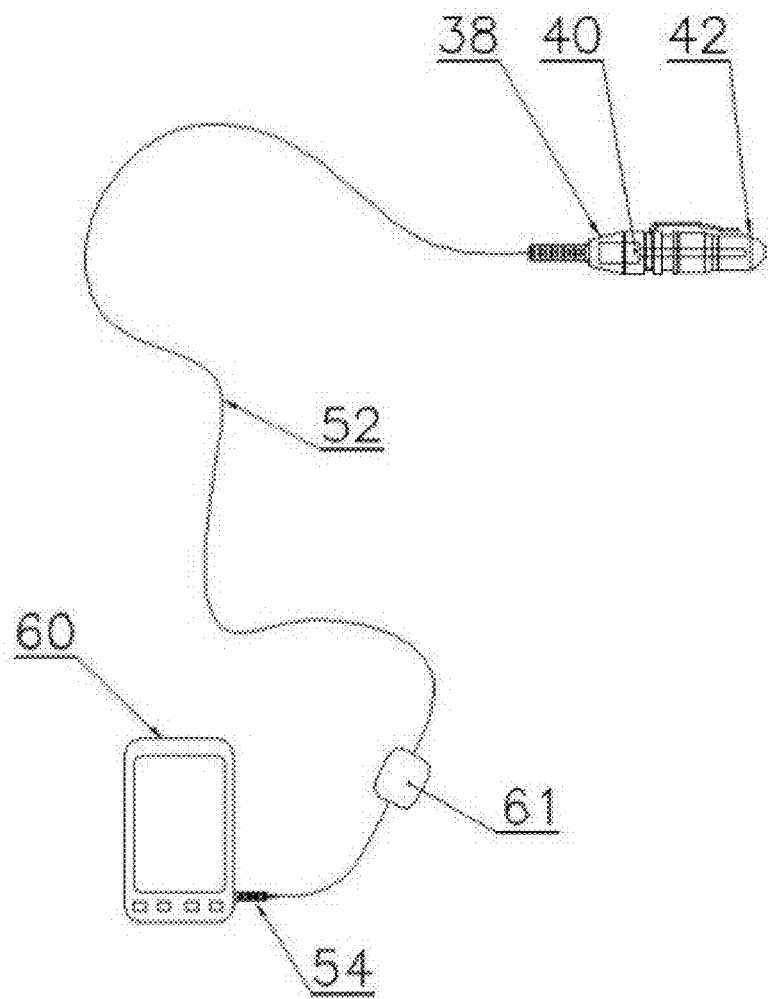
FIG. 4 illustrates one embodiment of the invention capable of being used with a mobile phone.

The example of another embodiment of the invention is represented by the use of a nasal applicator with mobile phone 60 (alternatively with computer 50) according to FIG. 4. The nasal applicator 38 is connected by connector 54 to the phone 60 (or to the computer 50). Then cable 52 follows, with control circuit 61 of laser diode 40 or without it. An application that allows changing or adjusting all parameters of treatment is installed in the mobile phone 60 (or in the computer 50). The treatment program can be adjusted in phone software. The type of polarization is by selection of the nasal adapter 42 and wave length for treatment is by selection of applicator 38.

Figure 5:
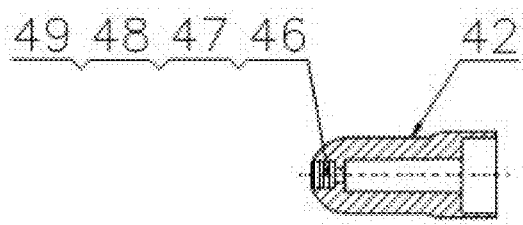
FIG. 5 illustrates a first embodiment of a nasal adapter according to an embodiment of the invention.
Figure 6:
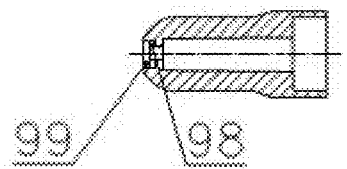
FIG. 6 illustrates a second embodiment of a nasal adapter according to an embodiment of the invention.
Figure 7:
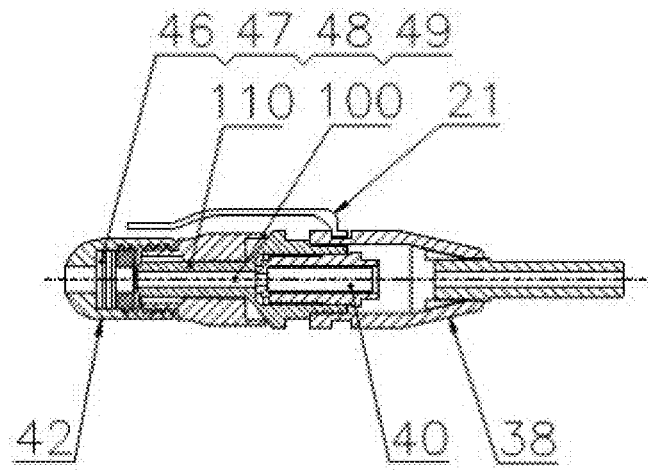
FIG. 7 illustrates a first embodiment of a nasal applicator according to an embodiment of the invention.

The design solution of the nasal applicator is clear from FIGS. 5-7. The nasal applicator 38 is with laser diode 40, with optic fiber 100, or with cavity without optic fiber 100 in intermediate piece 110. The intermediate piece 110 can be hollow, or with inserted optic fiber 100. The nasal adapter 42 is slipped over the intermediate piece 110. It includes the device for the generation of circular or elliptical polarization, that is, piece of glass 46, piece of glass 49, polarizer 47, quarter-wave plate 48, polarization foil 99, rubber pad adhesive on both sides or adhesive layer 98, while this device can be installed from the inner side of the nasal applicator or from its outer side using a different manner of its fixation to the nasal adapter 42. Pieces of glass 46, 49 can have the shape of lenses for the formation of the shape of light and for the protection of polarizer 47 and quarter-wave plate 48 included between pieces of glass 46, 49.

Figure 8:
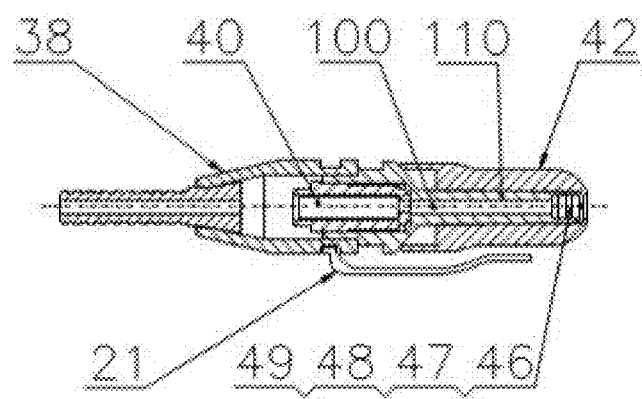
FIG. 8 illustrates a second embodiment of a nasal applicator according to an embodiment of the invention.

An alternative structural design of the nasal applicator is clear from FIG. 8. The nasal applicator 38 with intermediate piece 110, with or without optic fiber 100, with nasal adapter 42 at end of the intermediate piece 110 the device is intended for generation of circular polarization, i.e. pieces of glass 46, 49 that can have the shape of lenses, polarizer 47 and quarter-wave plate 48

Figure 9:
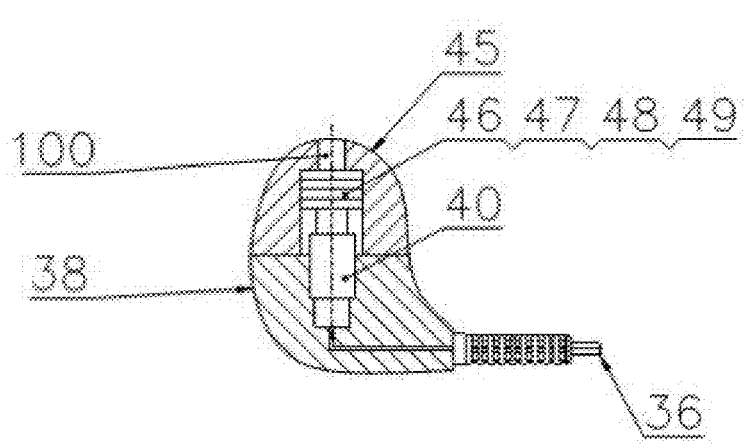
FIG. 9 illustrates a third embodiment of a nasal applicator according to an embodiment of the invention.
Figure 10:
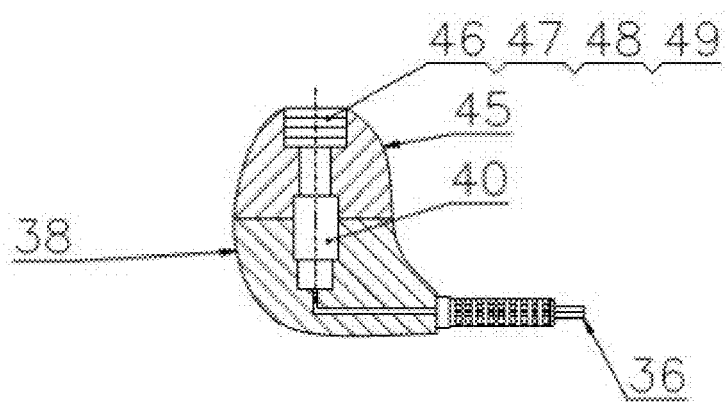
FIG. 10 illustrates a fourth embodiment of a nasal applicator according to an embodiment of the invention.

Additional embodiments of the nasal applicator pursuant to FIGS. 9-10 is represented by the nasal applicator 38 with laser diode 40 and device for generation of circular polarization by pieces of glass 46, 49, polarizer 47, quarter-wave plate 48 located immediately behind laser diode 40.

The main unit 1 intended for stimulation of the brain by laser circularly or elliptically polarized light allows creation of programs for power outputs of laser diode and frequencies of pulsations or interruptions of light, or they are pre-programmed in it, or they are transmitted to unit 51 from computer 50, or are created by the application in mobile phone 60.

The device for stimulation of the brain by laser circularly or elliptically polarized light can be used for research purposes, the prevention and therapy of cardiovascular and cerebrovascular diseases, hyperlipidaemia, and increased blood viscosity, consequences of injuries to brain, damage to organism due to the effects of increased viscosity, hyperlipidaemia and hyperglycemia, influences of life style, improvement of removal of waste substances accumulated in organism and in brain tissue, neurological diseases, disorders in behavior and concentration, seasonal affective disorder, anxieties and depressions, geriatric diseases, memory and intelligence, improvement of behavior, development of personality, and capabilities of the brain. It is also possible to anticipate its use in the therapy of tumors in achievable areas of the brain through the nasal cavity using substances that cause the photosensitivity of tumor tissues when suitable wave length of suitable power output is used, in order that tumor tissue is irradiated. The device can be used as a medical device in health care facilities and out-patient departments, as well as domestic treatment and nursing care within the framework of the prevention and therapy of diseases.

What is claimed is:

1. A device for stimulation of a brain, comprising:
a programmable control unit having a power source and a display, the power source capable of being controlled by engaging a button or by engaging the display; and
one or more applicators having an exit end, at least one applicator comprising one or more laser diodes;
wherein the programmable control unit is capable of storing a first set of parameters and a second set of parameters;
wherein the programmable control unit is capable of changing the first set of parameters to a second set of parameters;
wherein one or more applicators are supplied electrical energy;
wherein the laser diodes are capable of emitting polarized laser light to a nasal cavity or to an internal ear based on the second set of parameters; and
wherein at least one applicator comprises of a light plate adapter at the exit end, a removable adapter, and an intermediate piece capable of fitting with the removable adapter.

2. The device for stimulation of a brain of claim 1, wherein the laser light is circularly polarized.

3. The device for the stimulation of a brain claim 1, wherein wavelengths of one or more of the laser diodes is from 400 nm to 1,300 nm.

4. The device for the stimulation of a brain of claim 1, wherein the applicator is a nasal applicator.

5. The device for the stimulation of a brain of claim 4, wherein the light plate adapter comprises of a polarizer.

6. The device for stimulation of a brain of claim 4, wherein the light plate adapter comprises of a quarter-wave plate.

7. The device for stimulation of a brain of claim 4, wherein the light plate adapter comprises of a circular polarization foil.

8. The device for stimulation of a brain of claim 4, wherein the light plate adapter comprises of an adhesive layer.

9. The device for stimulation of a brain of claim 4, wherein the light plate adapter comprises of a glass plate.

10. The device for stimulation of a brain of claim 4, wherein the light plate adapter comprises of a lens shaped glass.

11. The device for stimulation of a brain of claim 4, wherein the nasal applicator is connected to the programmable control unit tangentially to a light axis.

12. The device for stimulation of a brain of claim 4, wherein the first set of parameters is adjustable by an external computing device.

13. The device for stimulation of a brain of claim 4, wherein the nasal applicator equipped with a laser diode is connected to the programmable control unit by at least one optic fiber.

14. The device for stimulation of a brain of claim 4, wherein the nasal applicator equipped with a laser diode is connected to the programmable control unit by at least one hollow tube.

15. The device for stimulation of a brain of claim 4,
   wherein the light plate adapter comprises a polarizer and
      a quarter-wave plate, such that the polarizer and the
      quarter-wave plate are located between two pieces of
      glass; and
   wherein the glass is manufactured with polarization of light.

16. The device for stimulation of a brain of claim 4, wherein the intermediate piece is covered by at least one adapter such that the adapter is capable of swiveling around a longitudinal axis.

17. The device for stimulation of a brain of claim 4, wherein at least one adapter is terminated at the exit end by elements that generate polarization.

* * * * *